United States Patent [19]
Maltby et al.

[11] 3,993,947
[45] Nov. 23, 1976

[54] ADMITTANCE MEASURING SYSTEM FOR MONITORING THE CONDITION OF MATERIALS

[75] Inventors: Frederick L. Maltby, Jenkintown; L. Jonathan Kramer, Devon; Kenneth M. Loewenstern, Warminster, all of Pa.

[73] Assignee: Drexelbrook Controls, Inc., Horsham, Pa.

[22] Filed: Sept. 19, 1974

[21] Appl. No.: 507,540

[52] U.S. Cl. ............................ 324/60 R; 324/57 R; 324/58 R; 324/58.5 R; 324/58 A
[51] Int. Cl.² .................. G01R 11/52; G01R 27/26
[58] Field of Search .............. 324/57 R, 58 R, 58 A, 324/58.5 R, 58.5 A, 60, 61, 58

[56] References Cited
UNITED STATES PATENTS

| | | | |
|---|---|---|---|
| 3,571,703 | 3/1971 | Russel | 324/60 R |
| 3,624,541 | 11/1971 | Lundstrom | 324/61 R |
| 3,646,434 | 2/1972 | Norwich | 324/61 R |
| 3,648,165 | 3/1972 | Shawhan | 324/60 R |
| 3,706,980 | 12/1972 | Maltby | 324/61 R |
| 3,746,975 | 7/1973 | Maltby | 324/61 R |
| 3,778,705 | 12/1973 | Maltby | 324/61 R |

*Primary Examiner*—Saxfield Chatmon, Jr.
*Attorney, Agent, or Firm*—Woodcock Washburn Kurtz & Mackiewicz

[57] ABSTRACT

An intrinsically safe system for monitoring the condition of materials includes a low power, stable frequency RF oscillator of the class C type comprising a resonant circuit which is coupled to a bridge network including the admittance of materials between a probe electrode and a grounded support member juxtaposed to the materials. The output of the network generates an AC error signal which is applied to a phase sensitive detector including a chopper and a low power chopper drive for generating a DC signal representing the magnitude of the AC signal at a predetermined phase angle. The bridge network which may be linearly calibrated is isolated from the oscillator and the output error signal circuitry so as to allow the oscillator and the output error signal circuitry to float with respect to the grounded support member and the power supply associated therewith. The rms voltage across the admittance representing the condition of materials is limited so as to permit the system to comprise a two-wire transmitter wherein the sole source of power for the transmitter is derived from a 4–20 milliamp current drawn by the transmitter.

28 Claims, 19 Drawing Figures

ADMITTANCE MEASURING SYSTEM FOR MONITORING THE CONDITION OF MATERIALS

BACKGROUND OF THE INVENTION

This invention relates to RF admittance measuring systems for monitoring the condition of materials, and more particularly, to systems of this type which are adapted for use at remote locations.

Heretofore, two-wire transmitters have been utilized to monitor various conditions at a remote location. Typically, a two-wire transmitter at a remote location is connected in series with a power supply and load at another location through two transmission wires. As the condition being monitored at the transmitter varies, the effective series resistance across the transmitter varies so as to produce a change in the current drawn by the transmitter which represents (e.g., is generally proportional to) the condition being monitored. A two-wire transmitter of this type is designed for low power consumption since the amount of power available to the transmitter from the remotely located power supply may be limited. Furthermore, certain applications may require that the two-wire transmitter be "intrinsically safe" so as to permit its use in the monitoring of conditions in an explosive environment. Under these circumstances, low energy usually associated with low power consumption becomes important so as to preclude the possibility of ignition and explosion.

Although the state of the art in two-wire transmitters is adequate for monitoring various types of conditions, the prior art technology with respect to the RF admittance measurement is deficient for two-wire transmitters for the following reasons.

When measuring the RF admittance between a probe electrode and a reference surface such as a grounded vessel, the resistance in parallel with the capacitance between the probe electrode and the grounded vessel becomes very important from a power consumption standpoint. Heretofore, it has generally been assumed that shunt resistance is sufficiently small in a sufficiently large number of applications so as to render the power provided by the 4 milliamp current in a 4–20 milliamp two-wire transmitter system insufficient to power the two-wire transmitter. In other words, the shunt resistance alone might consume more power than is available at the 4 milliamp condition leaving little or no power to operate the circuitry of the transmitter.

Moreover, in order for an admittance measurement to be accurate, reliable phase-sensitive detection must be utilized. However, such reliability usually requires a substantial source of power which is inconsistent with the low power requirements of a two-wire transmitter as discussed above and the available power because of the shunt resistance. This combination of factors imposes severe restrictions on the power which is generally considered necessary to provide a reliable RF signal from a suitable oscillator. Similar restrictions are placed on the power generally considered necessary to assure that the phase detector operates with a high degree of reliability.

Another problem which is somewhat unique to admittance measurements is the isolation of the bridge network in which the unknown admittance being measured is connected. Typically, the unknown admittance being measured is from a probe electrode to ground as disclosed in Maltby et al U.S. Pat. No. 3,781,672 and Maltby U.S. Pat. No. 3,706,980, both of which are assigned to the assignee of this invention. However, a power supply at a location remote from the bridge network as in the case of a two-wire transmitter, may not be connected to ground in a manner compatible with the bridge network. It is therefore necessary to isolate the bridge network from the bridge power supply so as to permit the bridge network to be connected to ground regardless of the power supply circuit. Moreover, if the voltage across the unknown admittance were reduced to minimize power consumption, the signal representing the unbalance of the bridge network would require amplification. Accordingly, the problem exists of providing an isolated source of power for such amplification.

Other problems exist in assuring linear and stable calibration of the admittance measuring system. It is also important to provide a system which will work with various types of probes and various lengths of cables associated with the probes without adversely affecting the admittance measurement.

To a very large degree, the above-mentioned problems are encountered when the system for monitoring the condition of materials comprises a battery-operated unit rather than a two-wire transmitter. Under these circumstances, the available power is again limited.

SUMMARY OF THE INVENTION

It is an overall object of this invention to monitor the condition of materials at a remote location utilizing RF admittance measurements.

It is a more specific object of this invention to minimize the power consumption necessary in making the RF admittance measurements.

It is also a more specific object of the invention to provide an intrinsically safe system for measuring RF admittance measurements.

It is a still more specific object of this invention to provide a two-wire transmitter which is capable of operating from the power suplied by 4–20 milliamps of current which flows through the two transmission wires connecting the two-wire transmitter to a remotely located power supply.

In accordance with these objects, a particularly preferred embodiment of the invention comprises an admittance sensing probe including a sensing electrode adapted to detect the admittance of materials for monitoring the condition of the materials, an RF signal generator and a bridge network coupled to the RF signal generator. The bridge network includes the admittance detected by the probe such that the unbalance of the network corresponds to the condition of the materials being monitored while the RF signal generator applies a voltage of less than the $\sqrt{\;}\;2V$ rms across the admittance detected, where V is the voltage across the two-wire transmitter. Output means are coupled to the bridge network for changing the current flow drawn by the two-wire transmitter from 4 milliamps to 20 milliamps in response to the unbalance of the bridge network so as to represent the condition of the materials.

It is also a specific object of this invention to provide isolation between a floating power supply and the probe so as to permit the admittance of the materials to be measured between the sensing electrodes and a grounded member.

It is a further object of this invention to provide DC isolation which is not subject to high voltage breakdown.

In accordance with these objects, the preferred embodiment of the invention comprises means for DC isolating the bridge network from the RF signal generator and the output means. The DC isolating means may comprise a first transformer having a primary connected to the RF signal generator and a secondary forming part of the bridge network. The DC isolating means may further comprise a second transformer having a primary connected to the bridge network and a secondary connected to the output means.

In order to increase the output voltage from the bridge network before application to the output means, an amplifier means may be coupled to the output of the bridge network. In order to maintain isolation of the bridge network from the remainder of the two-wire transmitter and the remote power supply, the power supply for the amplifier is derived from the rectifying means coupled to the bridge network.

It is another object of this invention to provide for stable calibration of the admittance measurement.

In accordance with this object, the RF signal generator comprises an RF oscillator and a regulating circuit for the oscillator for maintaining the amplitude of the RF signal substantially constant. The regulating circuit comprises means for full wave rectifying the output of the oscillator and a capacitor coupled to the full wave rectifying means which is charged by current flow through the rectifying means. A voltage divider is connected between the capacitor and a control input of the oscillator so as to maintain the amplitude of the RF signal from the oscillator and the voltage across the capacitor substantially constant. By maintaining the amplitude of the RF signal substantially constant despite changes in the operating characteristics of the transistor within the oscillator and despite resistive loading from the sensing electrode of the probe to ground, stable calibration of the admittance measurement is attained.

In particularly preferred embodiment, the RF oscillator comprises a class C oscillator including a multivibrator and a resonant circuit so as to develop an undistorted RF sinusoidal signal while still limiting power consumption. The resonant circuit may comprise the aforesaid first transformer and the admittance in the bridge network.

In further accordance with the object of stable calibration and minimizing power consumption, the output means of the two-wire transmitter comprises a phase-sensitive detector including a chopper and a chopper drive means for generating a chopper trigger signal for application to the chopper means. The chopper drive means comprises a pair of field effect transistors having first and second channel electrodes and a gate electrode respectively and further comprises a pair of channel resistors. The first channel electrodes are interconnected and the second channel electrodes are connected to a source of regulated voltage through the channel resistors. The resonant circuit of the RF oscillator is coupled to the gate electrodes of each of the field effect transistors so as to render the field effect transistors alternately conductive. The channel resistors minimize power consumption by limiting the current flow through the pair of field effect transistors should the transistors be simultaneously conductive. In addition, the channel resistors which reduce the output voltage from channel electrode-to-channel electrode provide a sharper knee in the input-output curve at the threshold voltage of the field effect transistors so as to produce a more nearly square wave at the output and also limit or preclude any shift in the threshold voltage with temperature thereby enhancing the stability of the calibration. A feedback resistor between the interconnected channel electrodes and the gate electrodes is provided to achieve a duty factor of 50%.

The chopper drive means further comprises a second pair of field effect transistors comprising first and second channel electrodes and a gate electrode respectively with the first channel electrodes interconnected and the second channel electrodes being connected directly to the source of regulated voltage. A second pair of field effect transistors produces a square wave having a greater peak-to-peak voltage than the square wave output of the first pair of field effect transistors for use in driving the chopper. In order to minimize the power consumption, the second pair of field effect transistors are biased just above the threshold voltage of each transistor such that switching occurs at the zero crossing of the square wave generated by the first pair of field effect transistors. Since the second pair of field effect transistors are not on at the same time except for the instant of transition, virtually all current used by the second pair of field effect transistors is needed to drive the chopper and power consumption due to wasted current is minimized.

It is another object of the invention to provide an output means which maintains the stable current output for all current levels representing the admittance measurement.

In the preferred embodiment of the invention, the output means comprises an output amplifier including a voltage feedback network connected to a resistor through which the 4-20 milliamp DC current drawn by the two-wire transmitter flows so as to stabilize the flow of the 4-20 milliamp DC current at all current levels.

It is yet another object of this invention to provide a two-wire transmitter having a pair of terminals which may be interchangeably connected to the two transmission wires without damaging or adversely affecting the two-wire transmitter.

In accordance with this object of the invention, the input of the two-wire transmitter includes a full wave rectifying bridge permitting current flow through one pair of diodes when the terminals are connected to the transmission wires with one polarity and current flows through the other pair of diodes when the terminals are connected to the transmission wires with the opposite polarity.

It is also an object of this invention to provide for linear calibration of the admittance measurement.

In accordance with this object of the invention, the bridge network includes a span capacitance across which the unbalance of the bridge network is measured where the span capacitance is substantially larger than the capacitance of the admittance being measured. In a particularly preferred embodiment of the invention, the span capacitance is at least 10 times and preferably 25 times the capacitance of the admittance being measured.

It is a further object of this invention to provide for RF admittance measurements wherein the length of the cable connecting the probe electrode to the bridge network does not affect the measurement of the admittance.

In accordance with this object, the probe electrode may include a guard electrode juxtaposed to and shielding the probe electrode so as to maintain the potential of the guard electrode at substantially the same potential as the probe electrode for a given operating point where the probe electrode is connected to one side of the span capacitance through the axial conductor of a coaxial conductor and the guard electrode is connected to the other side of the span capacitance through the shield of the coaxial conductor.

In accordance with another object of this invention, the system may employ various types of probes including linear and non-linear immersion probes utilizing a guard electrode as well as a probe electrode.

In accordance with a still further object of this invention, the overall system is adapted for use in a battery operated mode or an AC supply mode.

BRIEF DESCRIPTION OF THE DRAWINGS

FIGS. 2(a-c) are waveform diagrams utilized in describing the operation of the circuit of FIG. 2;

DETAILED DESCRIPTION OF A PARTICULAR EMBODIMENT

Figure 1:
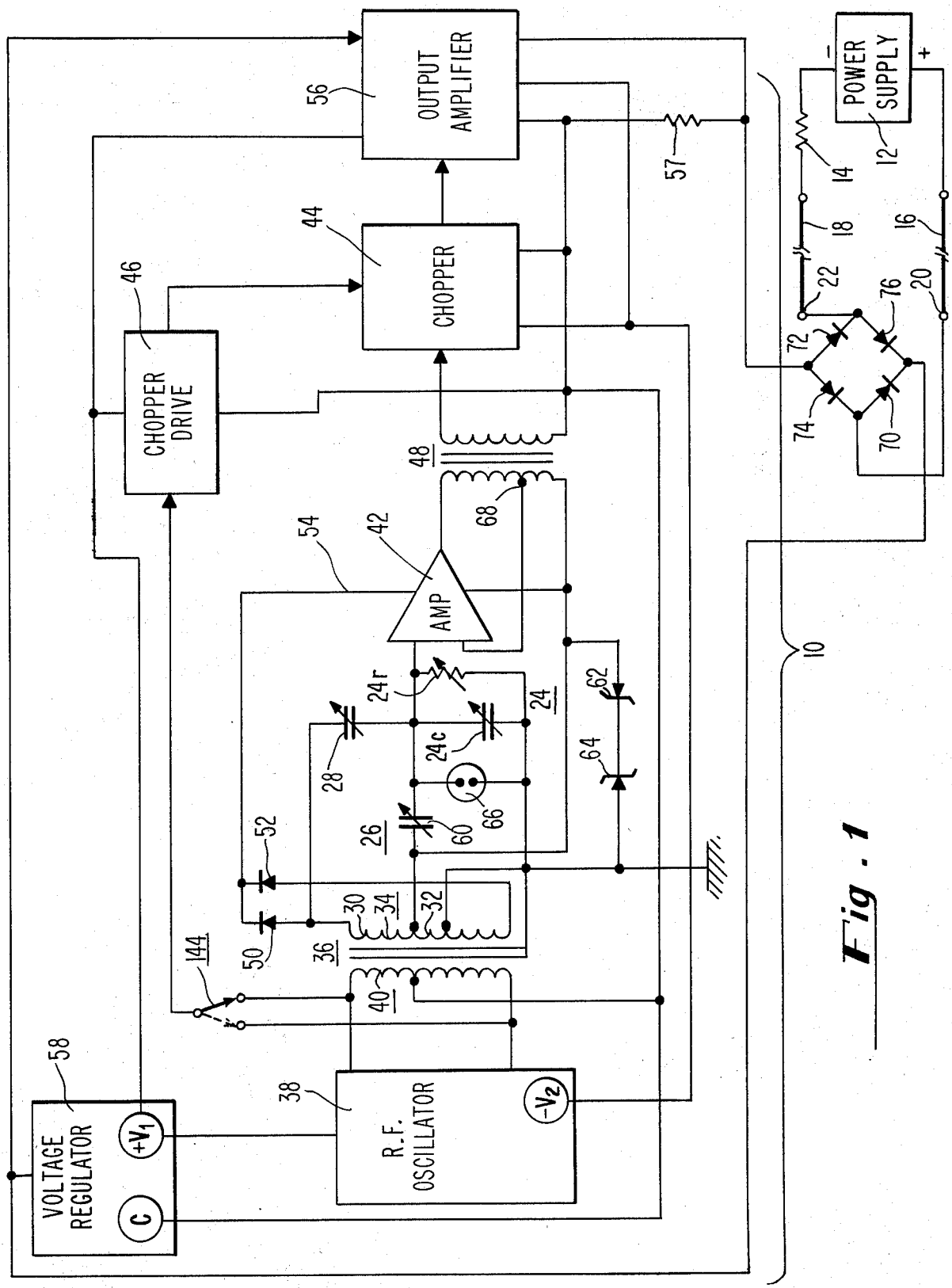
FIG. 1 is a block diagram of a two-wire transmitter embodying the invention.

As shown in FIG. 1, a two-wire transmitter 10 is connected in series with a power supply 12 and a load represented by a resistor 14 through transmission wires 16 and 18 connected to the terminals 20 and 22 of the two-wire transmitter 10. In accordance with this invention, the transmitter 10 is adapted to measure and draw a signal current representing an unknown measured admittance 24 which may represent the condition of materials sensed by the probe. The measured admittance 24 which represents the capacitance 24c and the resistance 24r from a probe electrode to ground forms one arm of a bridge network 26 also comprising a capacitor 28 and windings 30 and 32 of a secondary 34 in a transformer 36. The bridge network 26 is driven by an oscillator 38 having an output connected to the primary 40 of the transformer 36.

In accordance with this invention, the voltage across the admittance 24 is limited to a level so as to assure adequate power for the two-wire transmitter in view of the power consumption by the unknown resistance 24r. As will now be described in detail, the voltage is limited to less than $\sqrt{2V}$ where V is the voltage across the two-wire transmitter and the current drawn by the two-wire transmitter varies from 4–20 milliamps.

Heretofore, it has been assumed that the unknown resistance 24r of the unknown admittance 24 being measured may vary over a wide range. Of course, for a fixed voltage, if the resistance 24r should become very small, a good deal of power would be consumed in that resistance. In a conventional two-wire transmitter, the sole source of power is the current flow through the transmission wires 16 and 18 which is conventionally at levels of 4–20 milliamps. If it is assumed that the power supply produces an output voltage of 24 volts, the voltage across the terminals 20 and 22 of the two-wire transmitter may, for example, be 12 volts where the total voltage drop across the load 14 plus the drop across each of the wires 16 and 18 is 12 volts. This means that when the two-wire transmitter is drawing 4 milliamps, the total power available to operate the two-wire transmitter is P = VI = 48 milliwatts. This would mean that extremely small shunt resistances 24r would require extremely small voltages across the unknown admittance 24 to permit the two-wire transmitter to operate from the available power at the 4 milliamp level.

It has however been discovered, as will be described subsequently, that the resistance 24r, in almost all applications regardless of the type of probe utilized, will not fall below 500 ohms. Thus, by only moderately limiting the voltage across the unknown admittance 24 and thus the voltage across the unknown resistance 24r, sufficient power is available to the two-wire transmitter even at the 4 milliamp current level. Having once recognized that the magnitude of the resistance 24r will not, in almost all applications, fall below 500 ohms, the magnitude of the voltage across the resistance 24r may be readily computed for a 4–20 milliamp two-wire transmitter from the following equation:

$$\frac{v^2}{r_{24}} < VI_m \qquad (1)$$

where

V = the voltage across the transmitter;
v = the rms voltage across resistance 24r;
$I_m$ = the minimum current flow through the two-wire transmitter 10; and
$r_{24}$ = the resistance in ohms of the resistance 24.

For $I_m$ equal 4 milliamps and $r_{24}$ equal 500 ohms, then $$v < \sqrt{2V} \qquad 2.$$

If V equals 12 volts, then v is less than $\sqrt{24}$ or less than approximately 5 volts rms. Of course, the two-wire transmitter itself requires some power to operate. Therefore, in the preferred embodiment where $I_m = 4$ milliamps and V = 12 volts, v = approximately 2.2 volts rms, or substantially less than $\sqrt{2V}$.

In further accordance with this invention, the oscillator 38 of the class C type, i.e., the collector current of each of the two transistors in the oscillator 38 which drive the tank circuit flows through an angle less than 180° of the 360° cycle of the RF sinusoidal signal applied to the bridge network 26. However, class C operation may produce distortion in the intended sinusoidal signal. Therefore, in further accordance with this invention, the oscillator 38 comprises a resonant circuit in the form of a tank circuit including the transformer 36 as well as the measured admittance 24 as will subsequently be described in detail with reference to FIG. 2. Since the admittance 24 is part of the resonant circuit, little additional current is required to drive additional admittance between the probe and ground.

As also shown in FIG. 1, an AC error signal representing the unbalance of the bridge network 26 and thus the unknown measured admittance 24 is applied to an error amplifier 42. The error amplifier 42 permits the use of relatively low AC voltages in the bridge network 26 in accordance with this invention. The output from the error amplifier 42 is then applied to a phase sensitive detector comprising a chopper 44 which is triggered by a chopper drive 46.

In accordance with another important aspect of the invention, the bridge network 26 and the error amplifier 42 are isolated from the power supply by the first transformer 36 and the second transformer 48 which couples the output of the error amplifier 42 to the input of the chopper 44. In other words, the power supply is allowed to float with respect to the probe. This permits the use of a probe for measuring the admittance 24 between the probe electrode and ground without being concerned with the manner in which the power supply 12 is connected to ground. Note that this power supply 12 is at a remote location with respect to the two-wire transmitter 10 and the manner in which the power supply 12 is connected to ground may not be readily discernible at the two-wire transmitter 10. The isolation provided by the transformers 36 and 48 also allows either terminal 20 or 22 of the two-wire transmitter 10 to be maintained at a very substantial AC or DC voltage with respect to ground without any high voltage breakdown.

In order to provide isolation for the bridge network 26 while still providing a DC power supply for the error amplifier 42 which is directly coupled to the bridge network 24, diodes 50 and 52 are provided to rectify the RF sinusoidal signal from the secondary 34 of the transformer 36. Diodes 50 and 52 are then connected to a terminal 54 of the amplifier 42 so as to provide a DC power supply therefor which is isolated from the power supply 12.

In contrast, the DC power supply voltages for the RF oscillator 38, the chopper drive 46, the chopper 44 and an output amplifier 56 are provided by a voltage regulator 58 with a positive power supply terminal $+V_1$. In addition, a negative power supply voltage is provided by a voltage regulating circuit in the RF oscillator 38 at a terminal $-V_2$. The chopper drive 46, the chopper 44 and the output amplifier 56 are also connected to the circuit common terminal C of the voltage regulator 58.

In order to permit the bridge to be zeroed with a capacitance 24c from probe to ground which is different from the zeroing capacitance 28, the number of windings 30 differs from the number of windings 32. For example, the number of windings 30 may be three times as large as the number of windings 32 so as to allow the bridge to be zeroed when the measured capacitance 24c from probe to ground is three times as great as the zeroing capacitance 28. In addition, the bridge network 26 includes a variable span capacitor 60. By adjusting the span capacitor 60, the measured capacitance 24c necessary to produce a predetermined current through the transmission wires 16 and 18 may be varied. In addition, the output amplifier 56 may be provided with a gain adjustment which provides fine span control.

In order to provide spark protection for the transmitter 10, a pair of series connected, reversed poled Zener diodes 62 and 64 are connected between one terminal of the span capacitor 60 and ground. A neon bulb 66 is connected between the other terminal of the span capacitor 60 and ground. The protection afforded by the diodes 62 and 64 and the bulb 66 allow the transmitter 10 to withstand spikes of several thousand volts across the admittance 24 with no component failure or unbalancing of the bridge network 26.

As also shown in FIG. 1, a tap on the primary 68 of the transformer 48 is connected to the input of the error amplifier 42. This connection provides feedback to the amplifier 42 so as to control the gain thereof. Of course, changing the location of the tap 68 will change the gain of the amplifier 42 and thus the magnitude of the output applied to the chopper 44.

As the output from the chopper 44 varies and is compared with the voltage across a resistor 57 connected to the wire 22, the signal current output from the amplifier 56 is transmitted through the wires 16 and 18. The current having a magnitude which represents the admittance 24 and the condition of the materials being measured is utilized to drive the load 14.

In accordance with one aspect of the invention, the input of the two wire transmitter 10 comprises a full-wave rectifying bridge network comprising diode pairs 70 and 72 which conduct the 4–20 milliamp current when the terminal 20 is positive with respect to the terminal 22. Similarly, the pair of diodes 74 and 76 conduct when the terminal 22 is positive with respect to the terminal 20 or 22 to be connected to either transmission wire without damaging or affecting the operation of the transmitter.

The class C RF oscillator will now be described in detail with reference to FIG. 2. The oscillator comprises a multivibrator such as a pulsed amplifier including a pair of transistors 100 and 102 which are alternately conductive so as to drive a resonant tank circuit comprising the transformer 36 and a capacitor 104 which is connected in parallel with the primary 40 or the transformer 36 as well as the measured admittance A in the bridge network 26. The base drive for the transistor 100 of the multivibrator is provided by the capacitor 106 and resistors 108 and 110 where the resistor 110 is connected to a transistor 112 in a base current regulating circuit. Similarly, a capacitor 114 and resistors 116 and 118 provide a base drive for the transistor 102. The base current of the transistors 100 and 102 charge the capacitors 106 and 114 to a positive voltage higher than the supply voltage thereby cutting off the transistors 100 and 102 during most of the cycle so as to achieve class C operation. Diodes 120 and 122 which are connected in the base circuits of the transistors 100 and 102 respectively provide protection for the bases of the transistors by blocking current flow when the junction of the resistors 108 and 110 and the junction of the resistors 116 and 118 are driven positive.

As mentioned previously, the transistor 112 is part of a regulating circuit. The regulation afforded by the transistor 112 maintains the amplitude of the RF sinusoidal signals substantially constant despite any change in the operating characteristics of transistors within the oscillator and despite resistive loading due to the resistance 24r. In this connection, the base of the transistor 112 is connected to a tap in the voltage divider comprising resistors 124 and 126 with one terminal of the voltage divider connected to the $+V_1$ power supply terminal of the voltage regulator and the other terminal of the voltage divider connected to a capacitor 128 which is connected to circuit common through a discharge resistor 130 which may be potted with the capacitor 128 to provide intrinsic safety.

The capacitor 128 is charged to a negative potential with respect to circuit common by full wave rectifying diodes 127 and 129 connected across the tank circuit such that the tap of the voltage divider connected to the base of the transistor 112 is maintained at an operating point of approximately 0 volts which is just enough to render the collective-emitter circuit of the transistor 112 conductive. The emitter of the transistor 112 is maintained slightly negative by a resistor 132 and a diode 134. Diode 134 compensates for the base emitter voltage of the transistor 112 and partially compensates for changes in the base emitter voltage of the transistor 112 with temperature so as to assure stable calibration. As clearly shown in FIG. 2, the negative voltage of the capacitor 128 is utilized to provide a negative power supply voltage $-V_2$ for the chopper 44 and the output amplifier 56 as shown in FIG. 1.

The regulating circuit as previously described including the transistor 112 operates in the following manner to maintain the amplitude of the RF sinusoidal signal at the transformer 36 substantially constant. The voltage across the transformer 36 which is the voltage across the tank circuit of the oscillator is, in effect, detected by the diodes 127 and 129 which charge the capacitor 128. The resulting negative DC voltage on the capacitor is then compared to the voltage of the regulator 48 at the resistive voltage divider comprising the resistors 124 and 126 so as to maintain the intermediate tap at approximately circuit common. As the characteristics of the transistors change with temperature and the probe is resistively loaded as represented by the resistance $24r$, the transistor 112 leaks bias off the capacitors 106 and 114 so as to maintain the amplitude of the oscillator and the corresponding voltage across the capacitor at the same potential.

In order to eliminate any distortion in the RF sinusoidal signal, a relatively large choke inductor 136 provides a high impedance load to the tank circuit thereby avoiding any sharp current pulse which might distort the RF sinusoidal waveform. An inductor 140 and a capacitor 142 provides a power supply filter network.

The class C mode of operation for the oscillator 38 will now be described with reference to the waveforms of FIGS. 2 (a–c). As shown in FIG. 2a, the output voltage from the collector to circuit common which is applied across the primary 40 of the transformer 36 is substantially sinusoidal due to the resonant action of the primary 40 with the capacitor 104 and the image of the bridge capacitors 24c and 28 (shown on FIG. 6) reflected through transformer 40. However, the diode 120 is biased off by the voltage on capacitor 106 for most of the cycle, producing a voltage pulse as shown in FIG. 2c at the anode of diode 120. Thus, the collector current which flows through the transistor 100 is intermittent as shown in FIG. 2b. In fact, only a brief surge of collector current flows as shown in FIG. 2b during the 360° cycle depicted in FIG. 2a. (In actuality, some current continues to flow during the remainder of the cycle but this current is small relative to the surge of current flow and has not therefore been depicted in the drawing.) As shown in FIG. 2b, the substantial or surge of collector current flows for substantially less than 90° of the 360° cycle which is of course substantially less than 180° flow of current which still falls within the realm of class C operation. Note that the surge of current corresponds in time with the peak voltages for FIGS. 2a and 2c to assure that the maximum power is derived from the current flow.

Figure 2:
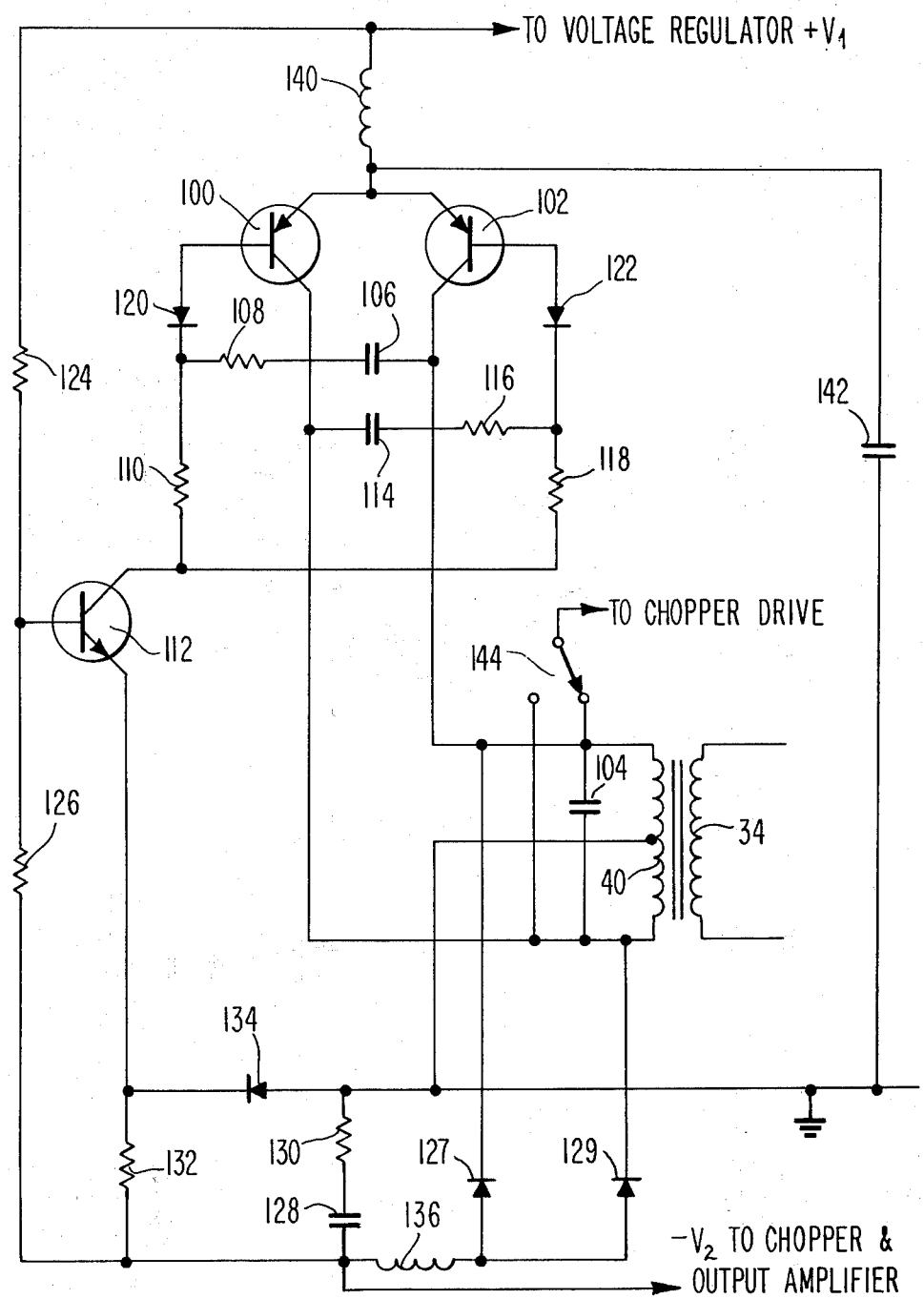
FIG. 2 is a schematic circuit diagram of an RF signal generator embodying one important aspect of the invention.
Figure 2A:
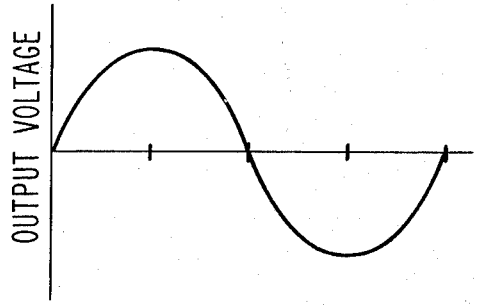
Figure 2B:
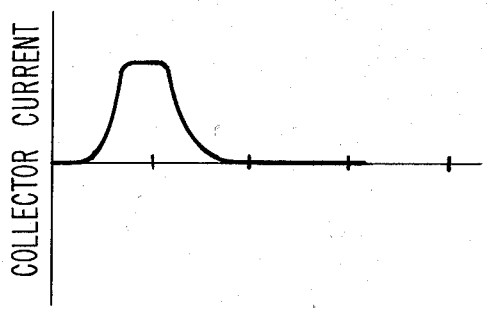
Figure 2C:
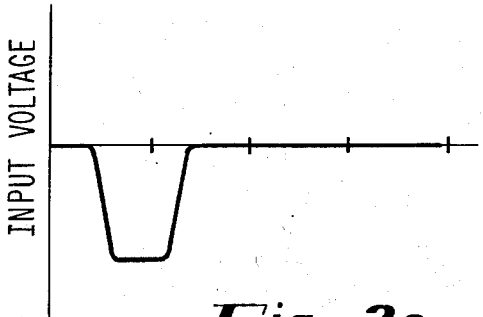

As shown in FIGS. 1 and 2, the tank circuit is connected to the chopper drive 46 through a switch 144 which is capable of connecting the chopper drive to either terminal of the primary 40. By moving the switch from one position to the other, the phase of the chopper drive is reversed 180° and the phase sensitive detection performed by the chopper 44 is changed by 180° to permit the transmitter to operate in a high level or low level failsafe mode. As will now be described in detail with reference to FIG. 3, the chopper drive 46 generates a square wave trigger signal for the chopper 44 while minimizing power consumption and optimizing stable, accurate calibration consistent with this invention.

Figure 3:
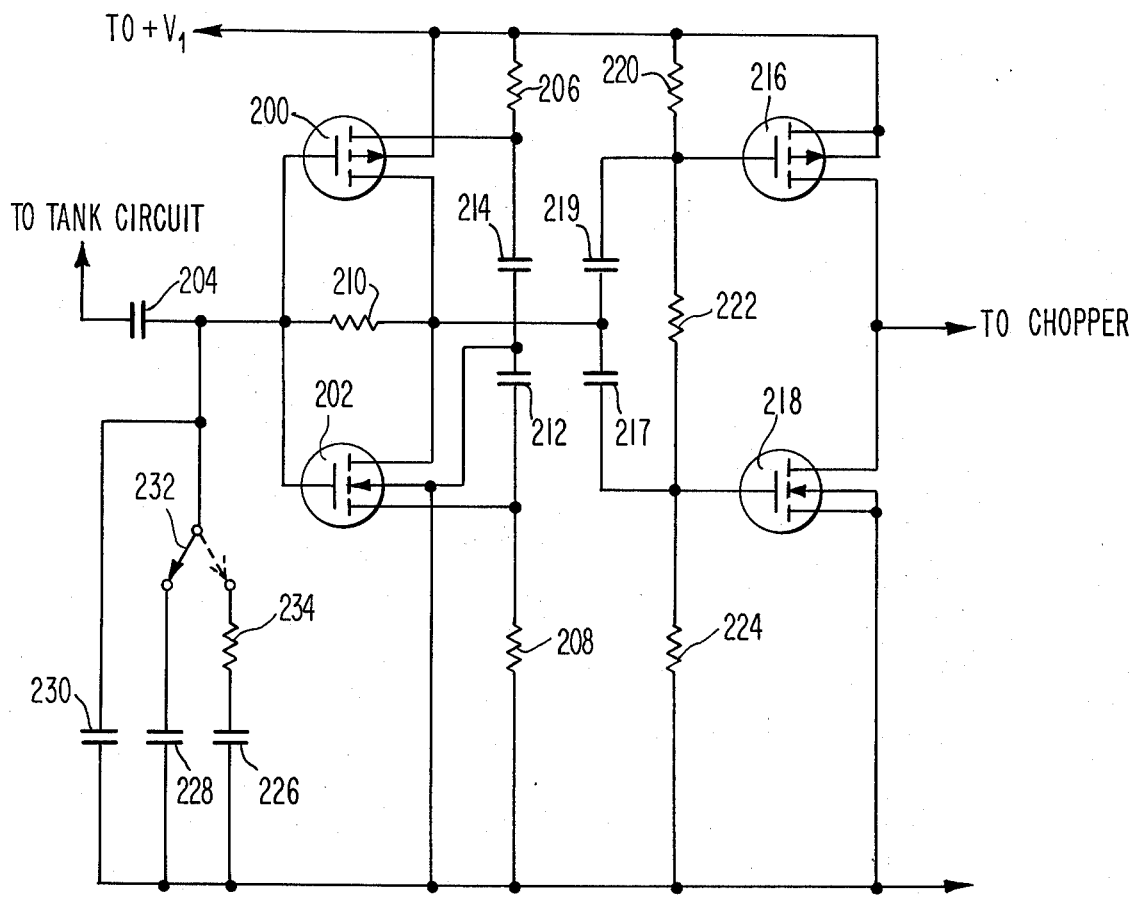
FIG. 3 is a schematic circuit diagram of a chopper drive circuit embodying another important aspect of the invention.

To achieve these objectives, chopper drive 46 as shown in FIG. 3 comprises a first pair of field effect transistors 200 and 202 having gate electrodes connected to the tank circuit through a capacitor 204. The first channel (drain) electrodes of the transistors 200 and 202 are interconnected and the second channel (source) electrodes are connected between circuit common and the regulated supply voltage $+V_1$. In accordance with the objectives of this invention, the second channel electrodes are connected to the power supply voltage $+V_1$ and circuit common through resistors 206 and 208.

The sinusoidal output from the oscillator 38 as shown in FIG. 1 is applied to a capacitive divider network including the capacitor 204 and capacitors 228 and 230 connected between the capacitor 204 and circuit common. The capacitively divided sinusoidal signal across the capacitors 228 and 230 is then applied to the gate electrodes of the transistors 200 and 202 to alternately gate the transistors between the conductive states.

Figure 3A:
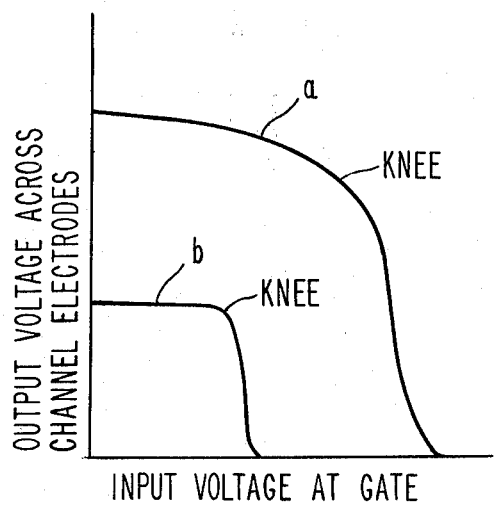
FIGS. 3a and 3b are input voltage - output voltage transfer characteristic curves of the field effect transistors of FIG. 3.

It will be understood that the resistors 206 and 208 play a particularly important role in assuring low power consumption and accuracy in the phase detection at the chopper 44. In this connection, it will be understood that the resistors 206 and 208 serve to limit the voltage across the channel electrodes of each of the transistors 200 and 202 which in turn sharpens the knee of the input voltage-output voltage transfer characteristics of the field effect transistors. As shown in curve $a$ of FIG. 3a, large output voltages from channel-electrode-to-channel-electrode of a field effect transistor give a rounded knee to the output voltage-input voltage transfer characteristic while limiting the output voltage as shown in curve $b$ sharpens the knee of the output voltage-input voltage characteristic. This tends to produce a more nearly square wave signal which is of the utmost importance in achieving reliability in the phase detection at the chopper 44.

Figure 3B:
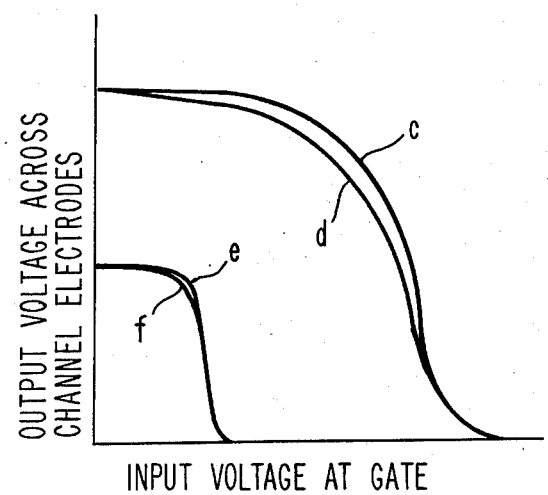

Moreover, as shown in FIG. 3b, limiting the output voltage of channel electrode to channel electrode of the field effect transistor tends to immunize the field effect transistor to changes in the output voltage-input voltage transfer characteristic with temperature. As shown in waveforms $c$ and $d$ of FIG. 3b where curve $c$ represents the output-input voltage characteristic at a temperature of −55° C. and curve d represents the output-input voltage characteristic at a temperature of +25° C. Thus, a large channel electrode-to-channel-electrode voltage makes for a very substantial difference in curves c and d which affect the stability of the calibrations for the system. On the other hand, limiting the output voltage as shown in curves e and f renders the −55° C. curve e substantially identical to the +25° C. curve f.

In addition, the channel resistors tend to limit current flow through the transistors 200 and 202 when the transistors 200 and 202 are simultaneously conductive between the first and second channel electrodes. This assures that the power consumption by the transistors 200 and 202 will not be excessive as in the case where both of the transistors 200 and 202 conduct simultaneously.

The output from the interconnected first channel electrodes is a square wave voltage riding above circuit common. In order to assure that the waveform is square, a feedback resistor 210 is provided between the first channel electrodes and the gate electrode so as to raise the gate electrode to the average DC voltage at the first channel electrodes. The resistor 210 assures a duty factor of 50% thereby compensating for small differences in the threshold voltages of the field effect transistors. Capacitors 212 and 214 provide a low impedance to drive the gate capacitance of the succeeding stage with the square wave signal generated by the field effect transistors 200 and 202.

Thus, the first stage of the chopper drive generates a voltage waveform which is square. However, the square voltage waveform is of insufficient peak-to-peak voltage to drive the chopper because of the voltage drop across the channel resistors 206 and 208.

Therefore, the succeeding or second stage of the chopper drive, which is AC coupled to the preceding stage through capacitors 217 and 219, comprises another or second pair of field effect transistors 216 and 218 which are biased near their respective threshold voltages by resistors 220, 222 and 224 which are connected to the gate electrodes thereof. By biasing the transistors 216 and 218 near their threshold voltages the transistors turn on very near the zero crossing of the square wave signal generated by the transistors 200 and 202. As a result, the duty factor of each of the transistors 216 and 218 more closely approaches 50% thereby eliminating any phase uncertainty so as to assure reliable phase detection at the chopper 44. Since the transistors 216 and 218 do not conduct simultaneously except for the instant of transition, there is little or no power wasted by the second stage.

Note that the transistors 216 and 218 are connected directly across the power supply voltage +$V_1$ and circuit common so that the output to the chopper 44 is alternately switched between +$V_1$ and circuit common. This produces a low output impedance in the chopper drive to assure fast rise and fall times of the resulting square wave output signal without the necessity of dissipating large amounts of power in the chopper drive. Accordingly, the square wave output signal generated by the field effect transistors 216 and 218 connected between the supply voltage $V_1$ and circuit common very closely approaches a perfect square wave so as to assure phase stability in the phase sensitive detection without sacrificing efficiency of the chopper drive.

Where a probe is utilized to measure the level of liquids and the liquids tend to coat the probe, it is desirable to provide means by which the phasing of the chopper drive square wave signal may be altered by a 45° lead. In this connection, it will be understood that long coatings on a probe as described in the aforesaid U.S. Pat. No. 3,706,980, which is incorporated herein by reference, appear as an infinite transmission line and the conductive and susceptive components of the coating are equal so as to produce a 45° lag. By detecting at a 45° phase angle, the conductive component and the susceptive component will cancel leaving only the susceptance due to the change in capacitance of the liquid level being measured and no susceptance due to the coating itself. In this connection, capacitor 226 and series resistor 234 or the capacitor 228 may be optionally connected in parallel with a capacitor 230.

Figure 4:
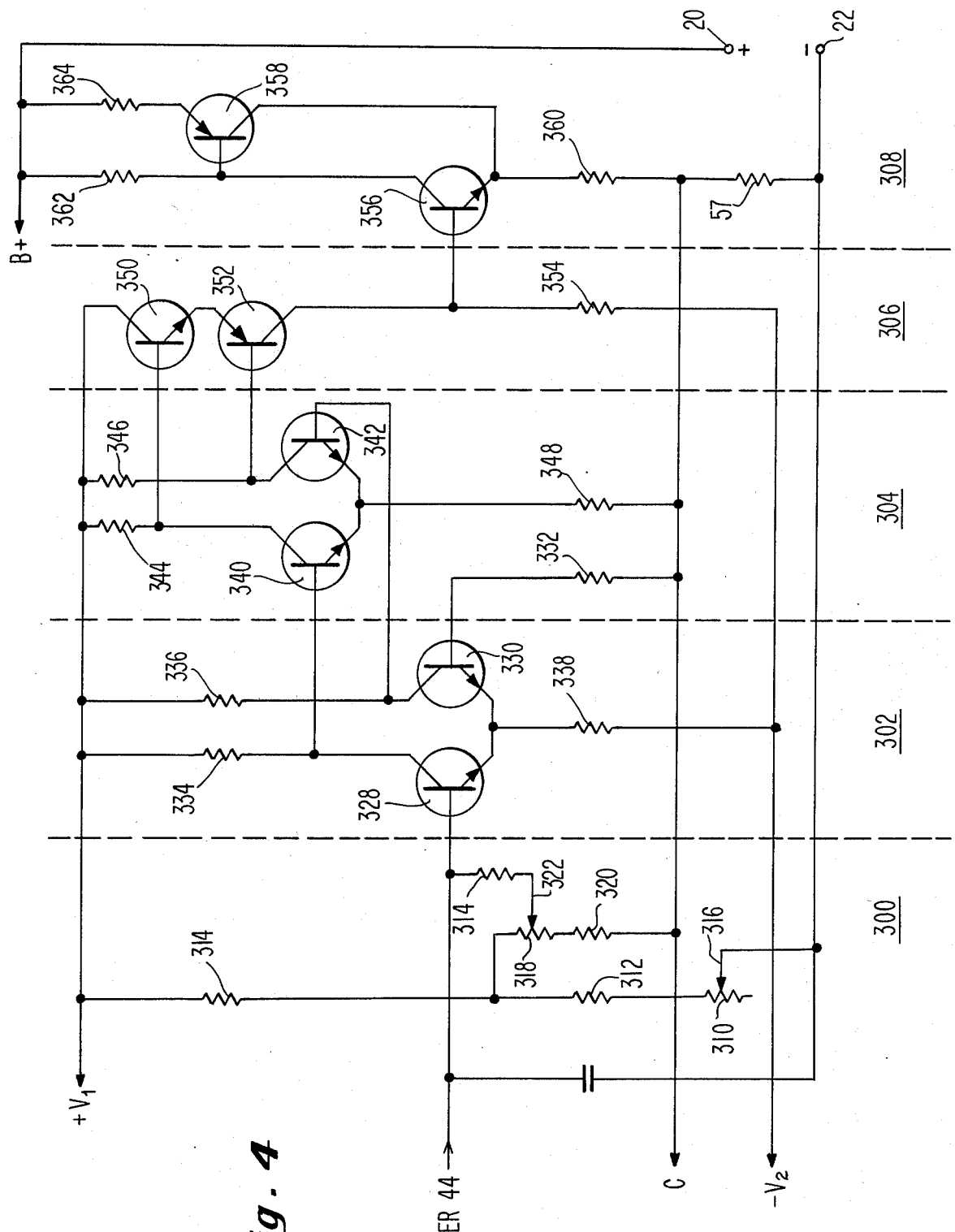
FIG. 4 is a schematic circuit diagram of an output amplifier embodying another important aspect of the invention.

In accordance with another important aspect of the invention, the output amplifier 56 comprises a voltage feedback network connected to a resistor 57 as shown in FIG. 1 through which the 4–20 milliamp DC current drawn by the two-wire transmitter flows so as to stabilize the flow of the 4–20 milliamp DC current at all current levels. As shown in FIG. 4, the output amplifier 56 is divided into the following sections: a voltage feedback divider network 300, a first differential amplifier stage 302, a second differential stage 304, a voltage to current gain stage 306 and an output amplifier stage 308 which is shown as including the resistor 57 connected between circuit common and the terminal 22 in FIG. 1.

The voltage feedback divider network 300 includes an independent point adjustment potentiometer 310 connected in series with resistors 312 and 314. A tap 316 on the potentiometer 310 is set so that when the bridge network 26 shown in FIG. 1 is at balance, the current drawn by the two-wire transmitter is 4 milliamps when no current is flowing through the gain adjustment network comprising a potentiometer 318 in series with a resistor 320 and having a adjustable tap 322 connected to the input of the first differential stage 302 through a resistor 324. When there is no current flowing through the gain adjustment network, the voltage with respect to circuit common C at the tap 322 remains at 0 volts throughout the entire range of gain control.

The differential amplifier stage 302 comprises a first transistor 326 having a base connected to the output from the chopper 44 and the voltage feedback network 300. The base of a second transistor 330 is connected to circuit common C through a resistor 332. The differential amplifier stage 302 includes biasing resistors 334, 336 and 338 which are connected between the positive power supply terminal +$V_1$ and the negative power supply terminal −$V_2$.

The second amplifier stage 304 comprises a first transistor 340 having a base connected to the collector of the transistor 328 and a second transistor 342 having a base connected to the collector of the transistor 330. Biasing resistors 344, 346 and 348 are connected between the positive power supply terminal +$V_1$ and circuit common.

The collectors of the transistors 340 and 342 are connected to the bases of a pair of transistors 350 and 352 of the voltage to current stage 306. The collector-emitter circuits of the transistors 350 and 352 are connected in series with a resistor 354 between the power supply terminal +$V_1$ and the negative power supply terminal −$V_2$.

The output stage comprises a pair of transistors 356 and 358 where the base of the transistor 356 is connected to the junction of the resistor 354 and the collector of the transistor 352 in the voltage to current gain stage 306. The output current from the output stage 308 is connected to the resistor 57 through a resistor 360. Resistors 362 and 364 connect the collector and emitter of the resistors 356 and 358 respectively to the terminal 20 of the two-wire transmitter.

When an unbalance is created at the bridge network 26, the voltage output from the chopper 44 increases which tends to make the base of the transistor 328 more positive. This renders the transistor 328 more conductive and the transistor 330 less conductive which in turn causes the voltage at the collector of the transistor 328 to decrease and the voltage of the collector of the transistor 330 to rise. The voltages at the collectors of the transistors 328 and 330 are then applied as input to the bases of the transistors 340 and 342 causing the voltages at the collectors of the transistors 340 and 342 to increase and decrease respectively. This in turn causes the transistors 350 and 352 to become more conductive and increase the current flow through the resistor 354 thereby raising the base of the transistor 356 to a more positive voltage causing an increase in current flow from the output transistors 356 and 358.

Since all of the current from the output transistors 356 and 358 flows through the resistor 57, the voltage across the resistor 357 will increase with increasing current flow due to the unbalance of the bridge network thereby decreasing the voltage at the terminal 22 with respect to circuit common C. This in turn increases the negative voltage which is applied to the base of the transistor 328 through the voltage feedback divider network until that voltage is again zero volts thereby establishing a stable condition at the higher output current.

From the foregoing, it should be understood that the output amplifier 56 may be analogized to an operational amplifier having one input at the base of transistor 328 acting as a summing junction for the voltage from the output of the chopper 44 and the voltage of the voltage feedback divider network 300 and the other input at the base of the transistor connected to circuit common.

In accordance with another important aspect of the invention, the length of the cables associated with the probe will not affect the admittance measurements.

Figure 5:
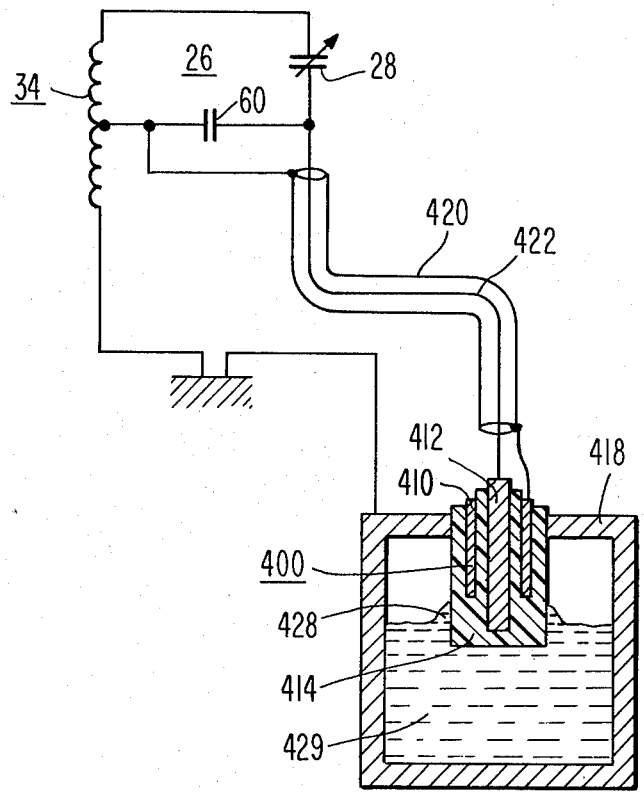
FIG. 5 is a schematic representation of the bridge network including a mechanical representation of the probe.

As shown in FIG. 5, a probe 400 is connected into the bridge network 26. The probe 400 includes a guard electrode 410 juxtaposed to and surrounding a probe electrode 412. Insulation 414 surrounds the probe electrode 412 so as to insulate the guard electrode 410 from the probe electrode 412 and the guard electrode 410 from a grounded conductive vessel 418. A coaxial cable is utilized to connect the probe 400 into the bridge network 402 where the shield of the cable 420 is connected to the guard electrode 410 at one terminal of the span capacitor 60 and the axial conductor 422 connects the probe electrode 412 to the other terminal of the span capacitor 60.

Figure 6:
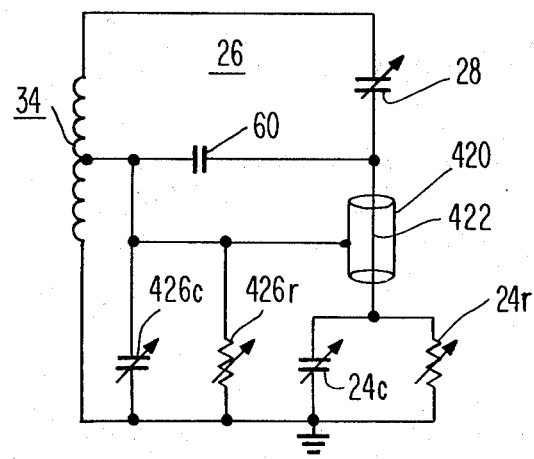
FIG. 6 is an equivalent circuit of the bridge network of FIG. 5.

Reference to FIG. 6, wherein the equivalent circuit of FIG. 5 is shown, reveals that a variation in the cable length will have no effect on the admittance measurement. As shown, the probe electrode to ground admittance 24 is represented by a capacitance 24c and a resistance 24r. Since the axial conductor 422 is surrounded by the coaxial shield 420 which is connected to the opposite terminal of the span capacitance 60, any admittance between the coaxial shield 420 and the axial conductor 422 will be connected across the span capacitance 60 and will not affect the balance or unbalance of the bridge network. Similarly, any admittance between the coaxial shield 420 and ground as represented by a capacitance 426c and a resistance 426r will have no effect on the balance of the bridge network 26 since this admittance is in parallel with the secondary 24 of the transformer.

In accordance with another important aspect of the invention, linear calibration of the admittance measuring system is achieved by making the span capacitance 60 large relative to the capacitance of the admittance being measured as disclosed in U.S. Pat. No. 3,778,705 – Maltby. Preferably, the capacitance of the span capacitor 408 or the span capacitor 26 is at least 10 times the capacitance of capacitance 424c or capacitance 24c. In a particularly preferred embodiment, the span capacitance is 25 times the capacitance being measured.

As shown in FIG. 5, the probe 400 comprises a probe electrode 412 which is completely surrounded with insulation 414. As also shown, the insulation 414 is coated with materials 428 contained within the vessel 418. As will now be explained, the probe electrode-to-ground resistance 24r will, in substantially all applications, be in excess of the previously mentioned 500 ohms even when the probe is covered with a coating 428 of conductive liquid 429 as shown in FIG. 5.

Figure 7A:
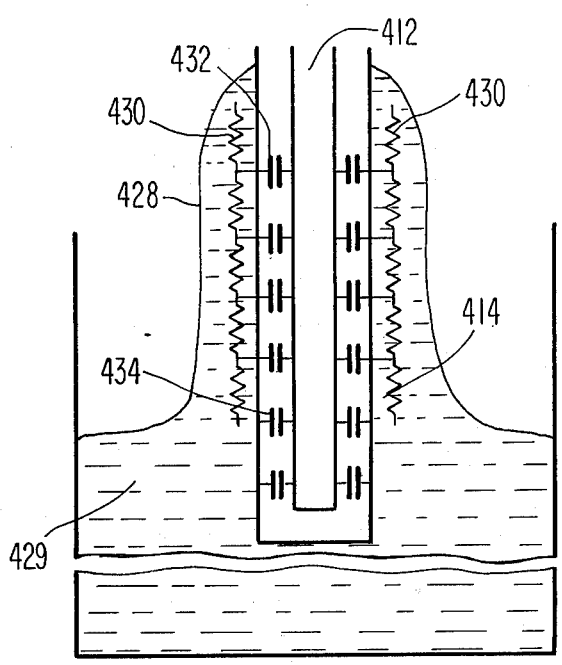
FIGS. 7(a-c) are schematic representations of various probes immersed in various materials.
Figure 8A:
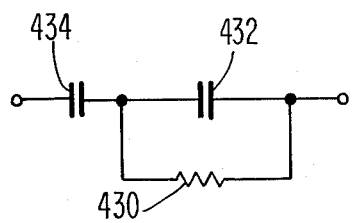
FIGS. 8(a-c) are equivalent circuits of the admittance measured by the probes of FIGS. 7(a-c) respectively.
Figure 9:
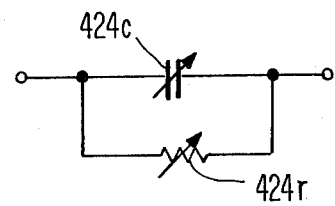
FIG. 9 is an equivalent circuit of the admittance of FIGS. 8(a-c)

Referring now to FIG. 7a, a schematic representation of the coating 428 on the probe 400 of FIG. 5 illustrates the nature of the probe-to-ground resistance. As shown there, the coating 428 may be represented by a series of small resistors 430 which are coextensive with the length of the coating. The junction of these resistors 430 are connected to the probe electrode 414 by shunt capacitors 432 which represent the capacitance of the insulation 414. An equivalent circuit corresponding to the probe and coating of FIG. 7a is illustrated in FIG. 8a wherein the capacitor 432 is connected in shunt with the resistor 430. A capacitor 434 represents the capacitance through the insulation 414 from the conductive liquid below the coating 428 to the probe electrode 412. This equivalent circuit may in turn be represented as shown in FIG. 9 by the shunt resistor 424r and the shunt capacitor 424c. It has been found that in substantially all applications where the resistance 424r as shown in FIG. 9 is contributed by the coating 428 as represented by the series of resistors 430 shown in FIG. 7a, the resistance 424r is more than 500 ohms.

Figure 7B:
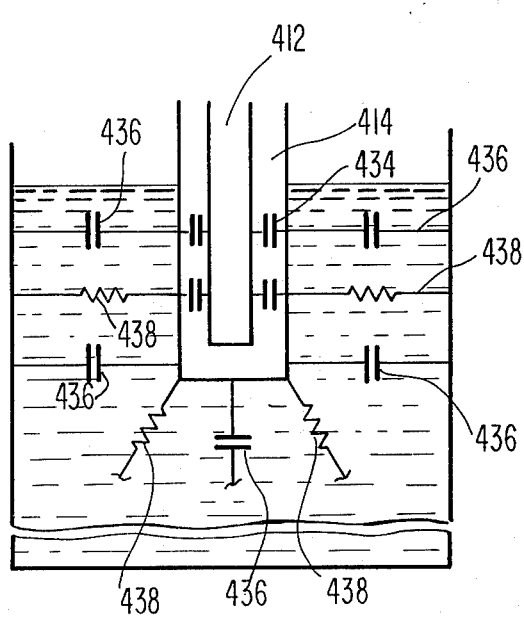
Figure 8B:
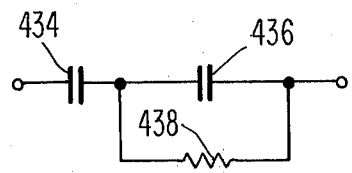

FIG. 7b represents the insulated probe 400 of FIG. 5 immersed in a semi-conductive liquid wherein the liquid itself is represented by a number of shunt capacitors 436 and shunt resistors 438. The equivalent circuit for the immersed probe of FIG. 7b is shown in FIG. 8b wherein the shunt capacitors 436 and the shunt resistors 438 are connected in parallel and a capacitor 434 again represents the capacitance through the insulation from the materials to the probe electrode 412. The equivalent circuit of FIG. 8b may of course also be depicted as a shunt resistor-capacitor combination as shown in FIG. 9. Although the resistor 438 is now contributed by the semi-conductive material rather than the coating as in the immersed probe of FIG. 7a, it has nevertheless been found that the equivalent resistance 424r as depicted in FIG. 9 will, in substantially all cases, exceed 500 ohms for the immersed probe of FIG. 7b.

Figure 7C:
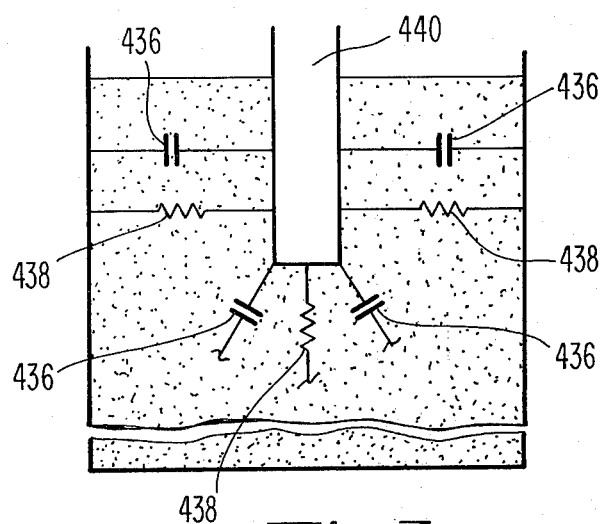

Finally, FIG. 7c depicts a bare probe 440 immersed in semi-conductive materials which may be represented by shunt capacitors 436 and shunt resistors 438 which are depicted in schematic circuit form by a resistance 442 and a resistance 444 in FIG. 8a. Once again, it has been found that the resistance 444 which represents the resistance 424r of FIG. 9 in the bridge network will exceed 500 ohms for almost all applications.

As described in the foregoing, the invention may be utilized with insulated as well as bare immersions probes including guard electrodes of the type described in Maltby U.S. Pat. No. 3,879,644 and incorporated herein by reference. It will of course be appreciated that the invention is equally applicable to two terminal probes without a guard electrode. It will also be understood that the invention is applicable to non-linear probes wherein the probe electrode is characterized, i.e., the cross-sectional dimension of the probe electrode varies from one end of the probe electrode to the other. Probes of this type are disclosed in Schreiber U.S. Pat. No. 3,269,180 which discloses a non-linear probe without a guard electrode and a non-linear probe with a guard electrode as disclosed in copending application Ser. No. 532,208 filed Dec. 12, 1974, assigned to the assignee of this invention, both of which are incorporated herein by reference. Furthermore, the invention is applicable to non-immersible probes which sense the condition of an admittance material when in close proximity therewith.

In the foregoing, the invention has been described in terms of a two-wire transmitter. It will of course be appreciated that many aspects of the invention may be embodied in other applications such as, for example a battery powered system, wherein the power available is as limited if not more limited than the two-wire transmitter application.

Figure 10:
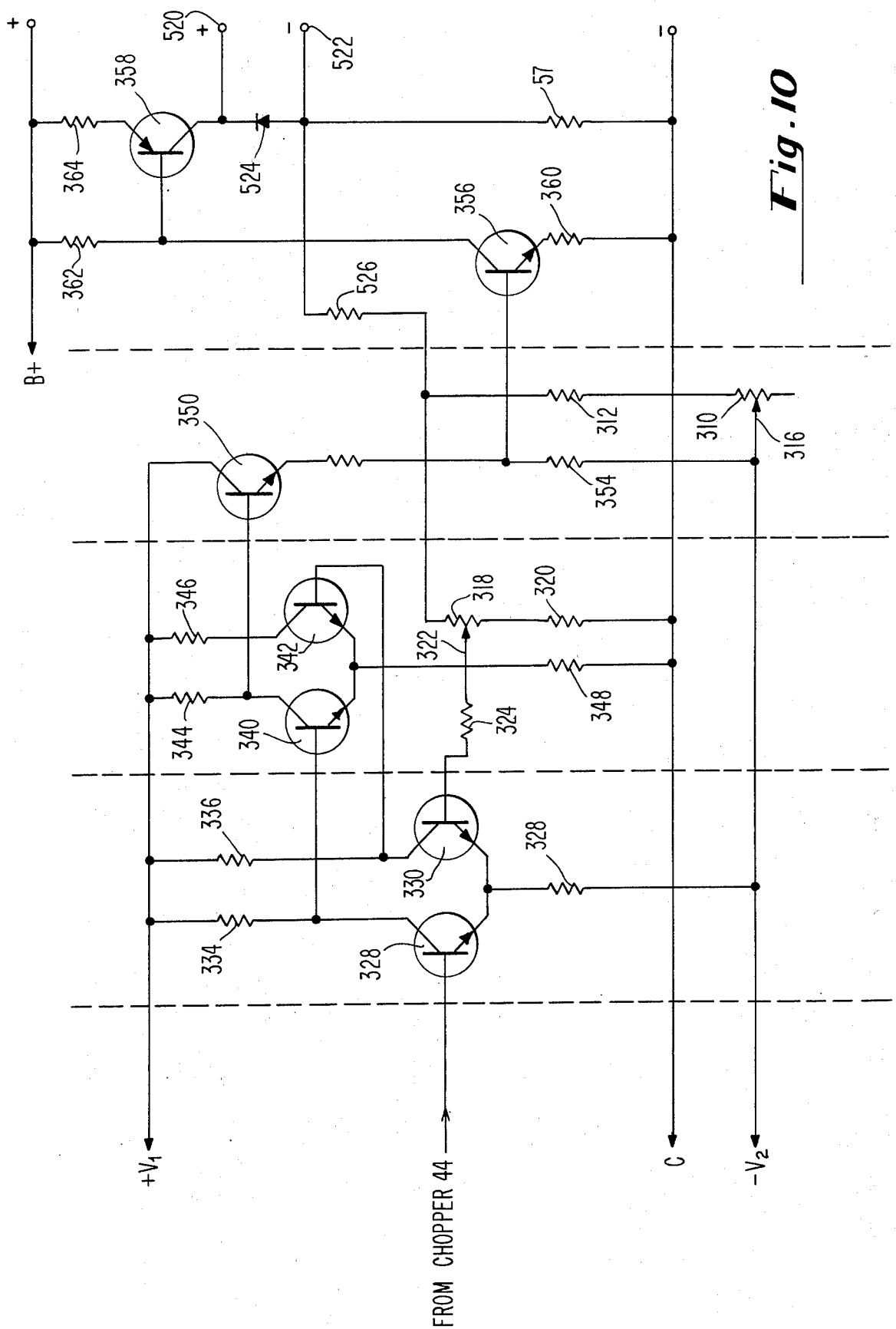
FIG. 10 is a schematic diagram of a battery-powered output amplifier.

In this connection, another output amplifier 56 for use in a battery powered system will now be described with reference to FIG. 10. As shown there, the output amplifier is in many respects similar to the output amplifier shown in FIG. 4 and substantially identical circuit elements bear identical reference characters.

However, the output amplifier of FIG. 9 differs in that the voltage feedback from the resistor 57 is not applied to a summing junction in the first differential amplifier stage but rather to the other input of the differential amplifier at the base of the transistor 330. The output signal is represented by the current flow and from output terminals 520 and 522 at the terminals of a diode 524 in the collector-emitter circuit of the transistor 358.

In operation, a positive input at the base of the transistor 328 and a first differential amplifier stage tends to increase the current flow through the resistor 57. This in turn raises the positive voltage applied to the base of the transistor 330 of the voltage divider network comprising the resistors 310, 312 and resistor 526. As a result, the current through the resistor 57 and the output current terminals 520 and 522 is stabilized at a higher current level.

It should be understood that the output amplifier described is in effect an operational amplifier having one input connected to the output of the chopper and the other input connected to a voltage feedback network as contrasted with the circuit of FIG. 4 wherein one input served as a summing junction connected to the chopper output as well as the voltage feedback network and the other input was connected to circuit common.

Although the chopper 44 has not been shown in detail, it will be understood that the chopper circuits and output amplifier circuits well known in the art are suitable for use in the two-wire transmitter system of this invention. For example, the chopper circuit disclosed in the aforesaid Schreiber U.S. Pat. No. 3,778,705 may be utilized. The output amplifier may comprise any of a number of commercially available differential amplifiers. It will also be understood that various resonant circuits may be utilized to replace the tank circuit shown in FIG. 1. Similarly, the voltage regulator circuit 58 may comprise a prior art voltage regulator well known in the art.

Although a preferred embodiment of the invention has been shown and described, it will be understood that various modifications may be made without departing from the true spirit and scope of the invention as set forth in the appended claims.

What is claimed is:

1. In a two-wire transmitter system comprising a power supply and a load at one location and a two-wire transmitter at another location interconnected by a pair of transmission lines carrying a variable signaling current in a signaling range having a minimum current of substantially 4 milliamps and powered solely by said power supply, the improvement residing in said two-wire transmitter comprising:
    an admittance sensing probe including a probe electrode adapted to detect the admittance of materials for monitoring the condition of the materials;
    an RF signal generator;
    a bridge network coupled to said RF signal generator, said bridge network including the admittance detected by said probe such that the unbalance of the network corresponds to the condition of the materials being monitored, said RF signal generator applying a voltage of less than the $\sqrt{2V}$ rms across the admittance detected where V is the voltage across the two-wire transmitter; and
    output means coupled to said bridge network for changing the current flow through the transmission lines in said signaling range in response to the unbalance of the bridge network so as to represent the condition of the materials.

2. The two-wire transmitter system of claim 1 including means for DC isolating said bridge network from said RF signal generator of said output means.

3. The two-wire transmitter system of claim 2 including amplifier means DC coupled to said bridge network and DC isolated from said RF signal generator and said output means.

4. The two-wire transmitter system of claim 3 including rectifying means coupled between said amplifier means and said bridge network for providing a DC power supply voltage to said amplifier while maintaining isolation between said amplifier and said power supply.

5. The two-wire transmitter system of claim 1 wherein said RF signal generator comprises an RF oscillator of the class C type including a resonant circuit so as to generate an RF signal characterized by a frequency equal to the resonant frequency of the resonant circuit.

6. The two-wire transmitter system of claim 5 wherein said DC isolation means comprises a transformer coupling the output of said oscillator to said bridge network, said transformer having a primary winding and a secondary winding, said primary winding, said secondary winding and the detected admittance forming part of said resonant circuit.

7. The two-wire transmitter system of claim 1 wherein said RF signal generator comprises an RF oscillator and a regulating circuit for said oscillator for maintaining the amplitude of said RF sinusoidal signals substantially constant despite resistive loading.

8. Thw two-wire transmitter system of claim 7 wherein said transmitter further comprises a voltage regulator and said regulating circuit includes means for full wave rectifying the output of said oscillator, a capacitor coupled to said full wave rectifying means and charged by current flow through said rectifying means, a voltage divider connected between said capacitor and said voltage regulator and control means coupled to said voltage divider and said oscillator so as to maintain the amplitude of said RF signal and the voltage across said capacitor substantially constant regardless of resistive loading across the detected admittance.

9. The two-wire transmitter system of claim 1 wherein said bridge network includes a span capacitance substantially greater than the capacitive component of the admittance detected by said probe so as to assure linear calibration of said transmitter.

10. The two-wire transmitter system of claim 1 wherein said output means comprises:
chopper means; and
chopper drive means having an input coupled to said oscillator and an output coupled to said chopper for applying a chopper trigger signal to said chopper.

11. The two-wire transmitter system of claim 10 wherein said chopper drive means comprises a first pair of field effect transistors comprising first and second channel electrodes and a gate electrode and a gate electrode respectively, and a pair of channel resistors, said first channel electrodes being interconnected and said second channel electrodes being connected across a source of voltage through said channel resistors so as to apply a reduced voltage across said first pair of field effect transistors, said RF signal generator being coupled to the gate electrodes of each of said field effect transistors so as to render said field effect transistors alternately conductive thereby generating a substantially square wave signal.

12. The two-wire transmitter system of claim 11 wherein said chopper drive means further comprises another pair of field effect transistors comprising first and second channel electrodes and a gate electrode respectively, said pair of channel electrodes being interconnected, said second channel electrodes being connected across said source of voltage and said gate electrode being connected to said first pair of transistors, said chopper drive means further comprising means for biasing said other pair of field effect transistors near the threshold values thereof such that the square wave signal generated by said first pair of field effect transistors is capable of turning said other pair of field effect transistors on at or near the zero crossing of said square wave signal without substantial simultaneous conduction of said other pair of transistors.

13. The two-wire transmitter system of claim 1 wherein said output means comprises:

a phase sensitive detector for generating a DC signal representing the unbalance of said bridge network; and
output amplifier means responsive to said DC signal and including a voltage feedback network responsive to the 4–20 milliamp DC current, said feedback network stabilizing the flow of said 4–20 milliamp DC current at all levels.

14. The two-wire transmitter system of claim 1 further comprising a full wave rectifying bridge at the input of said two-wire transmitter for connection to said pair of transmission lines so as to permit said two-wire transmitter to operate regardless of the polarity of the current applied to said two-wire transmitter.

15. The two-wire transmitter system of claim 1 wherein said sensing probe comprises a guard electrode surrounding said probe electrode, said guard electrode being connected to said bridge network so as to drive said guard electrode at substantially the same potential as said probe electrode at a given operating point.

16. The two-wire transmitter system of claim 15 further comprising a coaxial cable having an axially extending conductor surrounded by a coaxial shield, said shield connecting said guard electrode to one side of said bridge network and said axial conductor connecting said probe electrode to the other side of said bridge network.

17. The two-wire transmitter system of claim 16 wherein said bridge network further comprises a span capacitor connected from said one side of said bridge network to said other side of said bridge network, said output means being coupled to said bridge network to cross said span capacitance.

18. A system for monitoring the condition of materials comprising:
an admittance sensing probe including a probe electrode adapted to detect the admittance of materials;
an RF signal generator;
a bridge network coupled to said RF signal generator, said bridge network including the admittance detected by said probe such that the unbalance of the network corresponds to the condition of materials being monitored;
output means coupled to said bridge network for generating a signal in response to the unbalance of the bridge network so as to represent the condition of the materials; and
means for DC isolating said bridge network from said RF signal generator and said output means.

19. The system of claim 18 including an amplifier means DC coupled to said bridge network and DC isolated from said RF signal generator and said output means.

20. The system of claim 19 including rectifying means coupled between said amplifier means and said bridge network for providing a DC power supply voltage to said amplifier while maintaining isolation between said amplifier and said power supply.

21. The system of claim 18 wherein said DC isolating means includes a transformer having a primary coupled to said RF signal generator and a secondary forming part of said bridge network.

22. The system of claim 21 wherein said RF signal generator comprises an oscillator including a resonant circuit, said primary, said secondary and said detected admittance comprising part of said resonant circuit.

23. A system for monitoring the condition of materials in a two-wire system comprising a power supply and a load at one location and a two-wire transmitter at another location interconnected by a pair of transmission lines carrying a variable current, the improvement residing in said two-wire transmitter comprising:
  an admittance sensing probe including a probe electrode adapted to detect the admittance of materials for monitoring the condition of the materials;
  an RF signal generator comprising an oscillator including a resonant circuit, said resonant circuit including a bridge network including the admittance detected by said probe such that the unbalance of the bridge network corresponds to the condition of the materials being monitored; and
  output means coupled to said bridge network for changing the current flow through the transmission lines in response to the unbalance of the bridge network so as to represent the condition of the materials.

24. A system for monitoring the condition of materials comprising:
  an admittance sensing probe including a probe electrode adapted to detect the admittance of materials for monitoring the condition of the materials;
  a bridge network including the admittance detected by said probe when said unbalance of the bridge network corresponds to the condition of materials being monitored;
  an RF signal generator coupled to said bridge network and comprising an RF oscillator and a regulating circuit for said oscillator for maintaining the amplitude of said RF signals substantially constant, said regulating circuit including means for full wave rectifying the output of said oscillator, a capacitor coupled to said full wave rectifying means and charged by current flow through said rectifying means, a voltage divider connected between said capacitor and a regulated source of voltage and control means coupled to said voltage divider and said oscillator so as to maintain the amplitude of said RF signal and the voltage across said capacitor substantially constant; and
  output means coupled to said bridge network for generating an output signal in response to the unbalance of said bridge network so as to represent the condition of the materials being monitored.

25. The system of claim 24 wherein said RF oscillator comprises a multivibrator and a resonant circuit coupled to the output of said multivibrator.

26. In a two-wire transmitter system comprising a power supply and a load at one location and a two-wire transmitter at another location interconnected by a pair of transmission lines carrying a variable DC current, the improvement residing in said two-wire transmitter comprising:
  a pair of input terminals connected to said pair of transmission lines respectively;
  an RF signal generator;
  an admittance sensing probe including a probe electrode adapted to detect the admittance of materials for monitoring the condition of the materials;
  a bridge network coupled to said RF signal generator, said bridge network including the admittance detected by said probe such that the unbalance of the network corresponds to the condition of the materials being monitored;
  output means coupled to said bridge network for varying the DC current flow through the transmission lines; and
  a full wave rectifying bridge comprising four rectifying means coupling said input terminals to said output means, one pair of said rectifying means conducting when current flow through said transmission lines is of one polarity and the other pair of said rectifying means conducting when the current flow through said transmission lines is of the other polarity.

27. A system for monitoring the condition of materials comprising:
  an admittance sensing probe including a probe electrode adapted to detect admittance of the materials for monitoring the condition of the materials;
  an RF signal generator;
  a bridge network coupled to said RF signal generator, said bridge network including the admittance detected by said probe such that the unbalance of the network corresponds to the condition of the materials being monitored; and
  output means coupled to said bridge network for generating a signal representing the condition of the materials, said output means including chopper means and chopper drive means having an input coupled to said RF signal generator and an output coupled to said chopper for applying a chopper trigger signal to said chopper, said chopper drive means comprising a first pair of field effect transistors comprising first and second channel electrodes and a gate electrode respectively, a pair of channel resistors, said first channel electrodes being interconnected and said second channel electrodes being connected across the source of voltage through said channel resistors so as to apply a reduced voltage across said first pair of field effect transistors, said RF signal generator being coupled to the gate electrodes of each of the field effect transistors so as to render said field effect transistors alternately conductive thereby generating a substantially square wave signal.

28. The system of claim 27 wherein said chopper drive means further comprises a second pair of field effect transistors comprising first and second channel electrodes and a gate electrode respectively, said first channel electrodes being interconnected, said second channel electrodes being connected across said source of voltage and said gate electrodes being connected to said first pair of transistors, said chopper drive means further comprising means for biasing said second pair of field effect transistors near the threshold values thereof such that the square wave signal generated by said first pair of field effect transistors is capable of turning said second pair of field effect transistors on at or near the zero crossing of said square wave signal without substantial simultaneous conduction of said second pair of transistors.

* * * * *

UNITED STATES PATENT OFFICE
CERTIFICATE OF CORRECTION

Patent No. 3,993,947　　　　　Dated November 23, 1976

Inventor(s) Maltby et al

It is certified that error appears in the above-identified patent and that said Letters Patent are hereby corrected as shown below:

Column 9, line 15, the word "collective" should read --collector--.

Figure 8C:
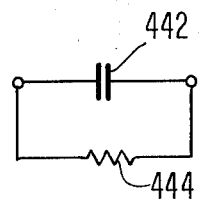

Column 15, line 7, "Fig. 8a" should read --Fig. 8c--.

Column 15, line 50, after the word "flow" insert --to--.

Column 15, line 59, after the word "and" insert --a--.

Column 17, line 11, change "Thw" to read --The--.

Signed and Sealed this

Eighth Day of March 1977

[SEAL]

Attest:

RUTH C. MASON
Attesting Officer

C. MARSHALL DANN
Commissioner of Patents and Trademarks

REEXAMINATION CERTIFICATE (1742nd)
United States Patent [19]
Maltby et al.

[11] B1 3,993,947
[45] Certificate Issued    Jul. 14, 1992

[54] ADMITTANCE MEASURING SYSTEM FOR MONITORING THE CONDITION OF MATERIALS

[75] Inventors: Frederick L. Maltby, Jenkintown; L. Jonathan Kramer, Devon; Kenneth M. Loewenstern, Warminston, all of Pa.

[73] Assignee: Drexelbrook Controls, Inc., Horsham, Pa.

Reexamination Request:
No. 90/002,406, Aug. 21, 1991

Reexamination Certificate for:
Patent No.: 3,993,947
Issued: Nov. 23, 1976
Appl. No.: 507,540
Filed: Sep. 19, 1974

Reexamination Certificate B0 3,993,947 issued.

Certificate of Correction issued Mar. 8, 1977.

[51] Int. Cl.$^5$ ............... G01R 27/26; G01R 11/52
[52] U.S. Cl. ................................. 324/610; 324/680; 324/651; 340/870.16
[58] Field of Search ............... 324/649, 650, 651, 652, 324/688, 663, 666, 668, 673, 675, 680, 682, 683, 690, 691, 693, 706, 708, 717, 610; 340/870.16

[56]           References Cited
U.S. PATENT DOCUMENTS 3,646,588  2/1972  Frick .
3,648,165  3/1972  Shawham .
3,680,384  8/1972  Grindheim .
3,706,980  12/1972 Maltby .
3,778,705  12/1973 Maltby .
3,781,672  12/1973 Maltby et al. .

FOREIGN PATENT DOCUMENTS
1528167  9/1975  United Kingdom .

OTHER PUBLICATIONS

"2-Wire Temperature Transmitters Offer Design Benefits," pp. 34–35, Control & Instrumentation, Feb. 1972.
Rosemount Engineering Co., Ltd., Bulletin E70–001, Nov. 1971.
Control & Instrumentation, Sep. 1970, p. 57, "Liquid Level Transmitter".
Industrie Post, Jan. 1, 1971, p. 22 with verified English Language Translation.

*Primary Examiner*—Jack B. Harvey

[57]           ABSTRACT

An intrinsically safe system for monitoring the condition of materials includes a low power, stable frequency RF oscillator of the class C type comprising a resonant circuit which is coupled to a bridge network including the admittance of materials between a probe electrode and a grounded support member juxtaposed to the materials. The output of the network generates an AC error signal which is applied to a phase sensitive detector including a chopper and a low power chopper drive for generating a DC signal representing the magnitude of the AC signal at a predetermined phase angle. The bridge network which may be linearly calibrated is isolated from the oscillator and the output error signal circuitry so as to allow the oscillator and the output error signal circuitry to float with respect to the grounded support member and the power supply associated therewith. The rms voltage across the admittance representing the condition of materials is limited so as to permit the system to comprise a two-wire transmitter wherein the sole source of power for the transmitter is derived from a 4–20 milliamp current drawn by the transmitter.

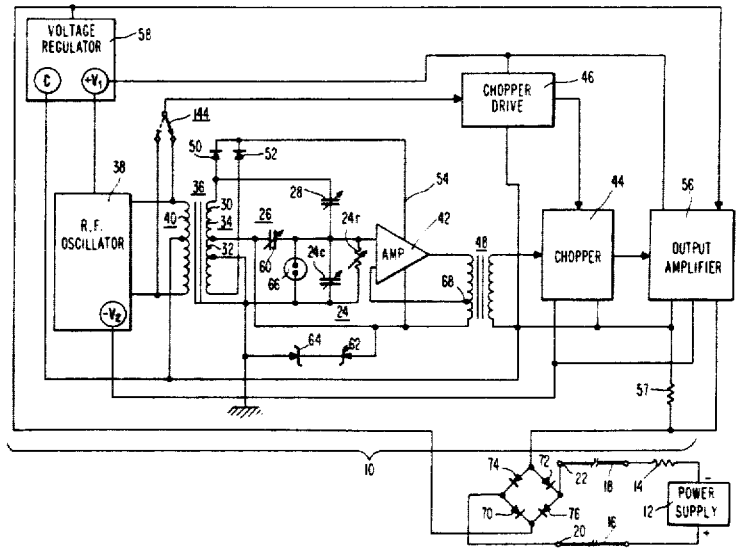

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1-28 is confirmed.

* * * * *